United States Patent
Little et al.

(10) Patent No.: US 7,759,619 B2
(45) Date of Patent: Jul. 20, 2010

(54) STERILISATION OF DUCT FLOWS

(75) Inventors: Richard Little, Southampton (GB); David Briggs, Reading (GB)

(73) Assignee: JenAct Limited, Hampshire (GB)

( * ) Notice: Subject to any disclaimer, the term of this patent is extended or adjusted under 35 U.S.C. 154(b) by 0 days.

(21) Appl. No.: 11/228,632

(22) Filed: Sep. 16, 2005

(65) Prior Publication Data

US 2006/0060577 A1    Mar. 23, 2006

(30) Foreign Application Priority Data

Sep. 17, 2004    (GB)    ................... 0420695.9

(51) Int. Cl.
*H05B 6/64* (2006.01)
*B01D 39/00* (2006.01)
*A61L 9/00* (2006.01)

(52) U.S. Cl. .............................. 219/679; 96/223; 422/4

(58) Field of Classification Search ................ 219/679, 219/601, 680, 678, 628; 96/224, 223, 225; 422/4; *H05B 6/64; B01A 39/00*
See application file for complete search history.

(56) References Cited

U.S. PATENT DOCUMENTS

| | | | |
|---|---|---|---|
| 3,911,318 A | 10/1975 | Spero et al. | 315/39 |
| 4,245,179 A | 1/1981 | Buhrer | 315/248 |
| 4,266,167 A | 5/1981 | Proud et al. | 315/248 |
| 4,507,587 A | 3/1985 | Wood et al. | 315/39 |
| 4,933,602 A | 6/1990 | Ono et al. | 315/39 |
| 5,015,349 A | 5/1991 | Suib et al. | 204/168 |
| 5,614,151 A | 3/1997 | LeVay et al. | 422/24 |
| 5,725,757 A | 3/1998 | Binot | 210/85 |
| 6,063,170 A * | 5/2000 | Deibert | 96/224 |
| 6,087,774 A * | 7/2000 | Nakayama et al. | 313/607 |
| 6,194,821 B1 | 2/2001 | Nakamura | 313/238 |
| 6,248,986 B1 * | 6/2001 | Tran et al. | 219/679 |
| 6,369,371 B2 * | 4/2002 | Havens et al. | 219/688 |
| 6,610,990 B1 | 8/2003 | Moruzzi | 250/504 R |
| 6,617,806 B2 * | 9/2003 | Kirkpatrick et al. | 315/248 |
| 6,673,137 B1 * | 1/2004 | Wen | 96/224 |
| 6,856,093 B2 | 2/2005 | Little et al. | 315/39 |
| 6,900,421 B2 * | 5/2005 | Varma | 219/679 |
| 7,081,637 B2 | 7/2006 | Waluszko | 250/504 R |
| 2002/0030453 A1 * | 3/2002 | Kirkpatrick et al. | 315/248 |
| 2002/0098109 A1 * | 7/2002 | Nelson et al. | 422/5 |
| 2003/0206683 A1 * | 11/2003 | Obee et al. | 422/121 |
| 2005/0264215 A1 | 12/2005 | Briggs et al. | 315/39.51 |

(Continued)

FOREIGN PATENT DOCUMENTS

DE    4010809    10/1990

(Continued)

OTHER PUBLICATIONS

U.S. Appl. No. 09/831,449 (particulars unknown; unpublished application).

(Continued)

*Primary Examiner*—Daniel L Robinson

(57) ABSTRACT

Sterilisation of airflow in a duct may be achieved by irradiating the air with light in the ultraviolet spectrum. Electrodeless bulbs may be enclosed in part of a duct and fed with RF energy in order to energize the bulb. The RF energy may be contained using grids dimensioned to be opaque to the selected RF wavelength.

6 Claims, 1 Drawing Sheet

U.S. PATENT DOCUMENTS

2007/0284315 A1    12/2007    Collins et al. ............... 210/748

FOREIGN PATENT DOCUMENTS

| | | |
|---|---|---|
| GB | 2048589 | 12/1980 |
| GB | 2307097 | 5/1997 |
| GB | 2399216 | 9/2004 |
| JP | 10015546 | 1/1998 |
| JP | 11-045684 | 2/1999 |
| JP | 2000-311568 | 11/2000 |
| RU | 2191443 | 10/2002 |
| WO | WO 00/32244 | 6/2000 |
| WO | WO 01/09924 | 2/2001 |
| WO | WO03/021632 | 3/2003 |
| WO | WO03/094982 | 11/2003 |

OTHER PUBLICATIONS

U.S. Appl. No. 11/903,690 (particulars unknown; unpublished application).

* cited by examiner

STERILISATION OF DUCT FLOWS

FIELD OF THE INVENTION

This invention relates to a duct steriliser and to a duct incorporating a steriliser.

BACKGROUND OF THE INVENTION

It is becoming increasingly important to kill bacteria and viruses in flows in ducting, for example, ducting used for airflows such as in air conditioning systems. It is known to use ultraviolet light in such applications.

SUMMARY OF THE INVENTION

In accordance with a first aspect of the invention there is provided a duct steriliser comprising a pair of apertured members adapted for spaced-apart placement across the flow direction of the duct to form a microwave enclosure in combination with the duct side walls, and at least one electrodeless discharge lamp arranged to radiate in the ultraviolet spectrum and for location in the enclosure.

In a second aspect, there is provided a duct incorporating the steriliser of the first aspect.

BRIEF DESCRIPTION OF THE DRAWINGS

Embodiments of the invention will now be described by way of example and with reference to.

DETAILED DESCRIPTION OF THE INVENTION

Figure 1:
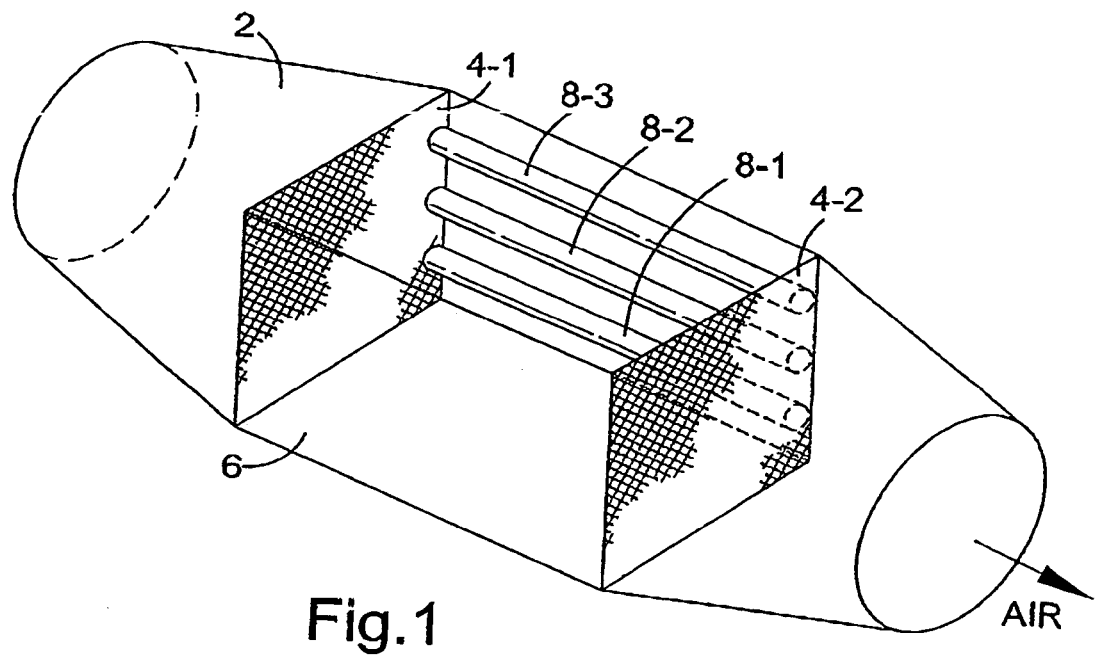
FIG. 1 which shows a cross-section through a first embodiment of the invention.

With reference to FIG. 1, a duct 2 is shown with air flowing from left to right across the page. The duct includes two members 4-1 and 4-2 which are apertured to allow air to flow through the duct. In this embodiment, the apertures are formed by creating the members from sheets of meshed or reticulated material.

In combination with the side walls of the duct, the apertured members 4-1 and 4-2 create an enclosure 6. Typically the duct walls and members will be made from electrically conductive material such as metal or will at least be plated with such material. Accordingly, with appropriate selection of the size of the apertures in the members 4-1 and 4-2, the enclosure 6 may be made to contain microwave energy. Thus by feeding microwave energy into the enclosure (not shown) and inserting a plurality of electrodeless bulbs 8-1, 8-2 and 8-3 into the enclosure, it is possible to strike the lamps and cause air passing through the enclosure to be exposed to ultraviolet radiation generated by the electrodeless discharge lamps in a microwave field.

It will be appreciated that since the bulbs are electrodeless, no shadowing occurs as a result of electrodes in the bulbs and furthermore no supply cables are required which would restrict airflow and create further shadowing. Furthermore, the complexity of mounting lamps in a duct with associated power supply cables is entirely avoided. Alternatively, the number of lamps which may be energized in the enclosure is not directly related to the number of power supplies as would be the case with typical low or medium pressure UV lamps. A single microwave power source may energies a plurality of lamps; further reducing complexity.

Figure 2:
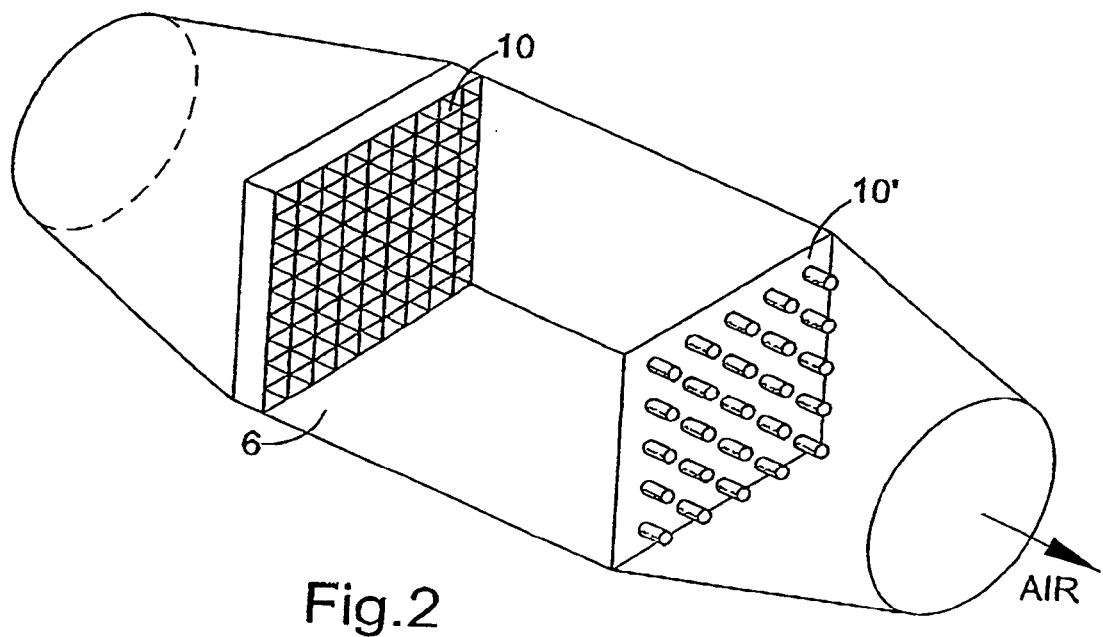
FIG. 2 which shows a cross-section of a second embodiment of the invention.

With reference to FIG. 2, an enhanced version is shown. It will be appreciated that the spacing and size of the apertures in the apertured members 4-1 and 4-2 will have an impact on the airflow through the duct. However, these characteristics are dictated by the operating microwave wavelength. FIG. 2 shows an alternative arrangement in which tubes 10 and 10' are used to allow air to flow through the duct whilst preventing transmission of microwave energy outside the enclosure 6. By using generally elongate tubes, it is possible to provide larger apertures and by ensuring that the tubes are beyond cutoff, still prevent microwave leakage. Generally, the length of the tubes should be greater than twice the maximum diameter or maximum cross-sectional dimension and should preferably be at least four times that dimension. Furthermore, the internal cross-sectional maximum dimension of each tube should be less than half the operating wavelength. Thus for a frequency of approximately 2.45 GHz, the maximum cross-sectional dimension of each tube should be not more than approximately 6 cm and each tube should preferably be at least 12 cm long. This, as is known to those skilled in the art, will create a tube which is beyond cutoff and will not transmit microwave energy. It will be appreciated that even for moderately high flow rates, such a tube presents little restriction in the duct 2 and indeed may assist with creating laminar flow within the duct.

With reference again to FIG. 2, it will be noted that at least two alternative constructions for the tubes are possible. The tubes 10 on the left of the figure are made in the form of a honeycombed apertured member with relatively thin members interlocking to form generally square or rectangular section holes. For example in the form of a reticulated reflector for a fluorescent luminere.

An alternative construction is shown for the apertured member 10' on the right of the figure, in which a series of generally cylindrical tubes are mounted on a generally planer surface. The skilled person will appreciate that many different constructions for the tube may be suitably manufactured. The critical features being the length and other dimensions relative to the operating wavelength, being chosen to ensure that the tubes (which operate according to waveguide theory) are beyond cutoff. For circular cross-section tubes, the cut-off length, $\lambda c$, is $3.412a$, where a is the radius. $\lambda_{cutoff}$ for a rectangular section tube for the lowest transmission mode is $2a$ where a is the largest cross sectional dimension.

Hence for an operating wavelength of 12 cm the broadest side of the rectangular cross section should not exceed 6 cm, and for circular guide the maximum diameter is 7.03 cm. In both cases these dimensions will block the transmission of the dominant mode and all higher modes.

The Figures show a generally cuboid enclosure. It will be appreciated that this is not an essential requirement and indeed the enclosure may for example be generally cylindrical.

Additionally the orientation of the bulbs in the cavity is not restricted and therefore the bulbs can be orientated in any direction in the cavity. The bulbs may also be of any required shape but are preferably cylindrical. One or more bulbs may be present in the cavity.

Preferably the enclosure is in the form of a resonant microwave cavity since this aids concentration of microwave energy for striking of the lamps.

The invention claimed is:

1. A duct steriliser comprising a pair of apertured members adapted for spaced-apart placement across an air flow direction of a duct to form a microwave enclosure in combination with the duct side walls, and at least one electrodeless discharge lamp arranged to radiate in the ultraviolet spectrum and for location in the enclosure, the enclosure being dimensioned and arranged to form a resonant cavity at an operating microwave wavelength, and wherein at least one of the apertured members includes a plurality of elongate tubes extending from and in registry with a respective plurality of the apertures in the member, the tubes having a length and width in relation to the operating microwave wavelength which prevents microwave energy passing through the tubes.

2. A steriliser according to claim 1, wherein the maximum cross-sectional internal dimension of each tube is less than $\lambda/2$ where $\lambda$ is the operating microwave wavelength, and wherein the length of each tube is greater than twice the maximum cross-sectional internal dimension.

3. A steriliser according to claim 1 arranged to operate generally at a frequency in the range of 2–3 GHz.

4. A duct incorporating the steriliser of claim 1.

5. A duct according to claim 4, wherein the duct is dimensioned to form a waveguide.

6. A sterilizer according to claim 3 wherein the frequency is 2.45GHz.

\* \* \* \* \*